US00PP37042P2

(12) United States Plant Patent
Murphy

(10) Patent No.: US PP37,042 P2
(45) Date of Patent: Oct. 21, 2025

(54) PERENNIAL PEANUT PLANT NAMED 'Murphy's Pintoi'

(50) Latin Name: *Arachis pintoi*
Varietal Denomination: Murphy's Pintoi

(71) Applicant: Travis Murphy, Fort Pierce, FL (US)

(72) Inventor: Travis Murphy, Fort Pierce, FL (US)

( * ) Notice: Subject to any disclaimer, the term of this patent is extended or adjusted under 35 U.S.C. 154(b) by 0 days.

(21) Appl. No.: 19/173,634

(22) Filed: Apr. 8, 2025

(51) Int. Cl.
*A01H 5/02* (2018.01)
*A01H 6/00* (2018.01)

(52) U.S. Cl.
USPC ..... Plt./258
CPC ..... *A01H 6/00* (2018.05)

(58) Field of Classification Search
USPC ..... Plt./258
CPC ..... A01H 5/02
See application file for complete search history.

*Primary Examiner* — Kent L Bell

(57) ABSTRACT

A new and distinct cultivar of *Arachis pintoi* plant named 'Murphy's Pintoi', particularly distinguished by small leaves, rapid and compact stoloniferous growth habit, infrequent flowering habit, low growth and dense foliage canopy.

6 Drawing Sheets

Genus and species: *Arachis pintoi.*
Cultivar denomination: 'Murphy's Pintoi'.

CROSS-REFERENCE TO RELATED APPLICATIONS

N/A.

ACKNOWLEDGEMENT OF FEDERAL RESEARCH SUPPORT

N/A.

BACKGROUND OF THE NEW CULTIVAR

*Arachis pintoi*, commonly known as Perennial Peanut, stoloniferous a perennial peanut or pinto perennial peanut belongs in the family Fabaceae and is native to Brazil. *Arachis pintoi* is related to two other species in the peanut genus *Arachis: A. glabrata*, also commonly known as Perennial Peanut, or rhizome perennial peanut, and *A. hypogaea*, the widely cultivated groundnut or "peanut". Both *A. pintoi* and *A. glabrata* were introduced into the U.S. in the middle half of the last century and have been extensively investigated and utilized for their high-quality forage and hay capacity in the animal husbandry industry. More recently both species have been investigated and are becoming more utilized for their capacity to provide an alternative to ornamental turfgrasses and ornamental ground covers in residential and commercial applications. The main difference between the two species is that *A. glabrata* generally spreads by rhizomes whereas *A. pintoi* spreads by stolons and seed. However, both species are able to form dense swards of vegetation. *Arachis repens*, also a stoloniferous perennial peanut, is a morphologically and genetically closely related species to *A. pintoi*. Both species belong to the same phylogenetic section, and they produce fertile hybrids. To the naked eye, both species appear identical. Only small, minor, morphological differences separate the two species.

The new *Arachis pintoi* variety 'Murphy's Pintoi' is the product of a breeding program conducted by the inventor in Ft. Pierce, Florida. The objective of the breeding program is to create and commercialize new low growing, sod-type and stoloniferous perennial peanut cultivars as a utility peanut and as an ornamental utility turf for landscaping.

SUMMARY OF THE INVENTION

The invention relates to a new and distinct cultivar of Perennial Peanut plant named 'Murphy's Pintoi'. 'Murphy's Pintoi' was discovered in 2019 as a single plant in a heterogenous cultivated field of unnamed and unpatented *A. pintoi* plants. The new Perennial Peanut variety was selected due to its small leaves, compact growth habit, infrequent and very sparce flowering habit, and dark green and dense foliage.

First asexual propagation of 'Murphy's Pintoi' by stolon vegetative divisions occurred in Ft. Pierce, Florida between June and October of 2019; since then, it has been asexually propagated by stolon vegetative divisions and has remained true-to-type for 4 or more generations.

Plant Breeder's Rights for the new cultivar 'Murphy's Pintoi' have not been applied for, and 'Murphy's Pintoi' has not been made publicly available more than one year prior to the filing date of this application.

The new cultivar 'Murphy's Pintoi' has not been observed under all possible environmental conditions. The phenotype of the new cultivar may vary with variations in environment and cultural practices such as temperature, light intensity, fertilization, irrigation, and application of plant growth regulators without any change in genotype.

The following are the most outstanding and distinguishing characteristics of 'Murphy's Pintoi' when grown under standard growing conditions under natural light in Ft. Pierce, Florida: small leaves, rapid and compact stoloniferous growth habit, infrequent flowering habit, low growth and dense foliage canopy.

'Murphy's Pintoi' originated in heterogeneous field of unnamed and unpatented *A. pintoi* plants. When compared to these heterogenous parent or progenitor plants, 'Murphy's Pintoi' is uniform and homogenous, has a much more compact growth habit, and has a dense and dark green canopy of foliage. The parent or progenitor plants overall have a more open growth habit and are less compact with lighter colored foliage.

DESCRIPTION OF THE FIGURES

This new cultivar 'Murphy's Pintoi' is illustrated by the accompanying photographs, which show the plant's form and foliage. The colors shown are as true as can be reasonably obtained by conventional photographic procedures. The photographs were taken in June 2024 and show approximately one-year-old plants grown in fields and in containers in Ft. Pierce, Florida and Quincy, Florida.

DETAILED BOTANICAL DESCRIPTION OF THE CULTIVAR

Figure 1:
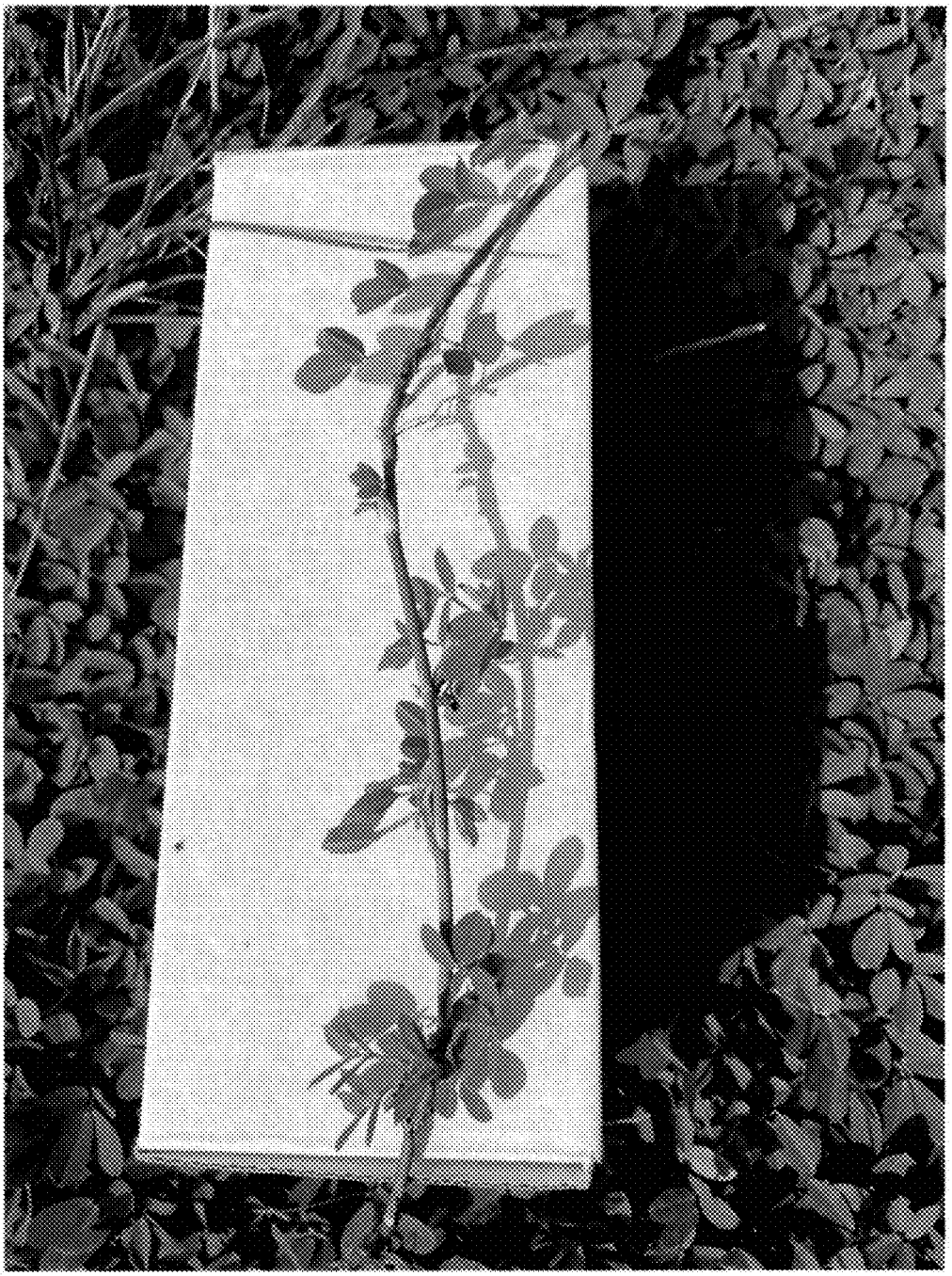
FIG. 1 shows a typical sprig of 'Murphy's Pintoi'.
Figure 2:
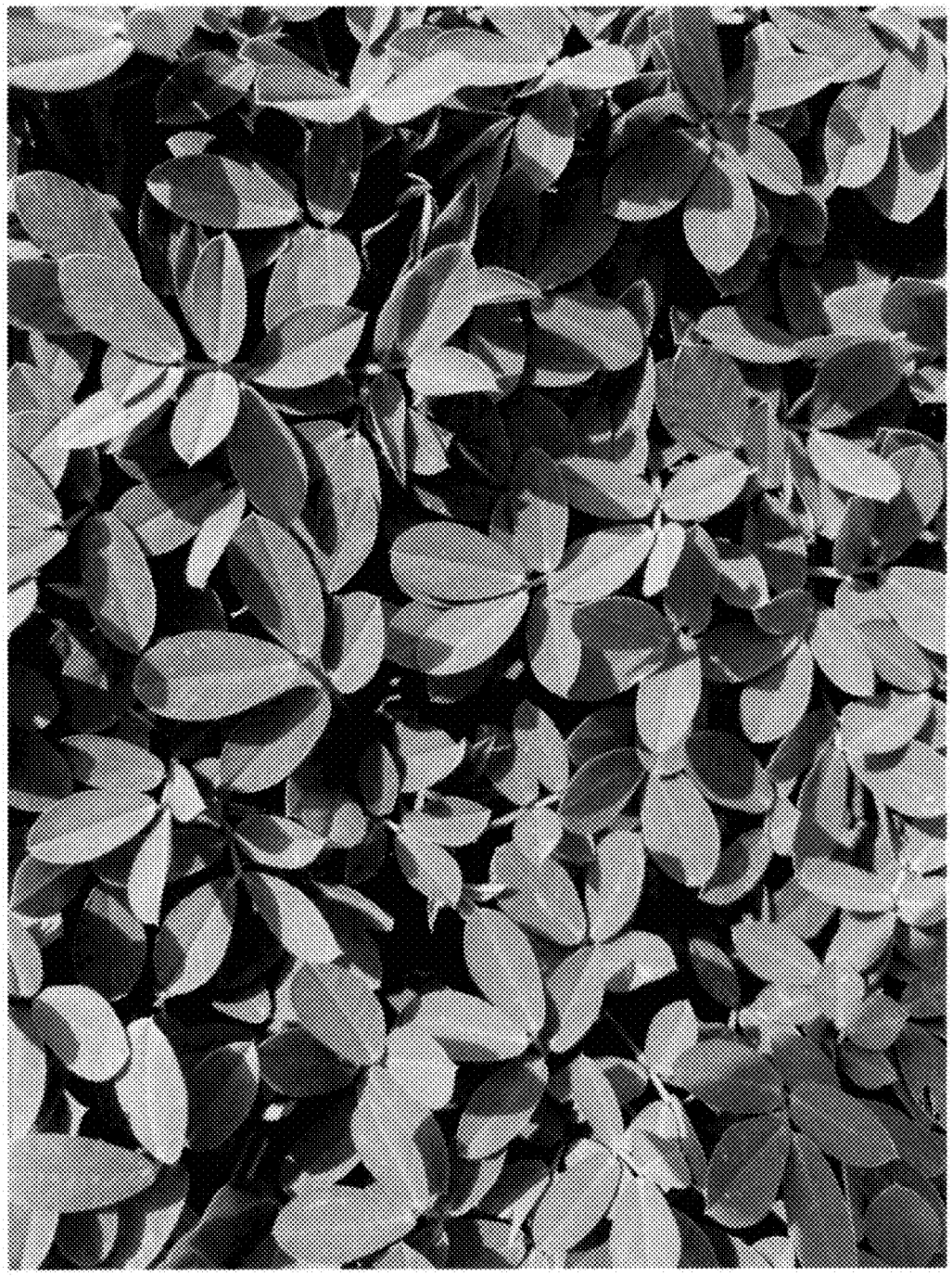
FIG. 2 shows a close up of typical foliage of 'Murphy's Pintoi'.
Figure 3:
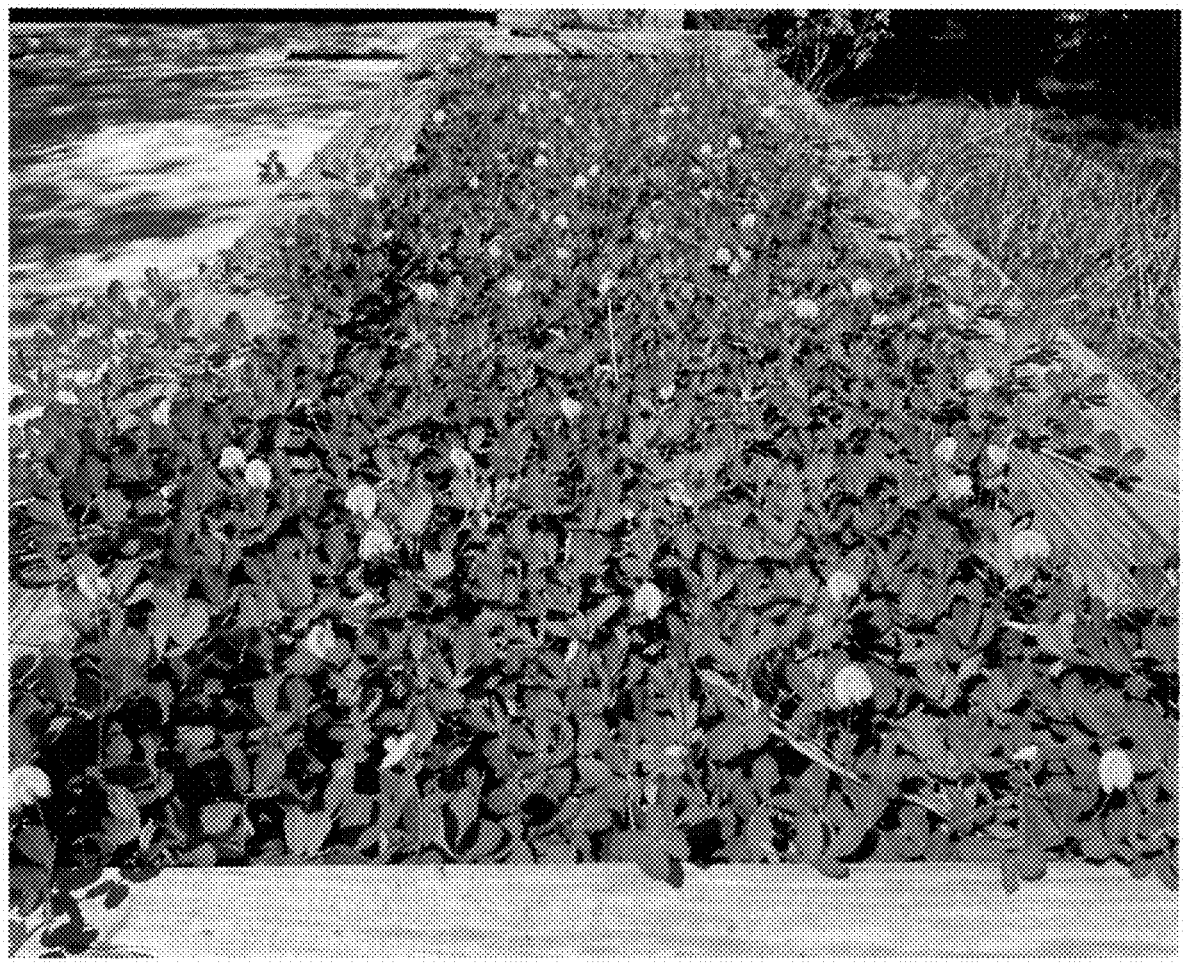
FIG. 3 shows the typical foliage and flowering habit of 'Murphy's Pintoi' when grown in container bed.
Figure 4:
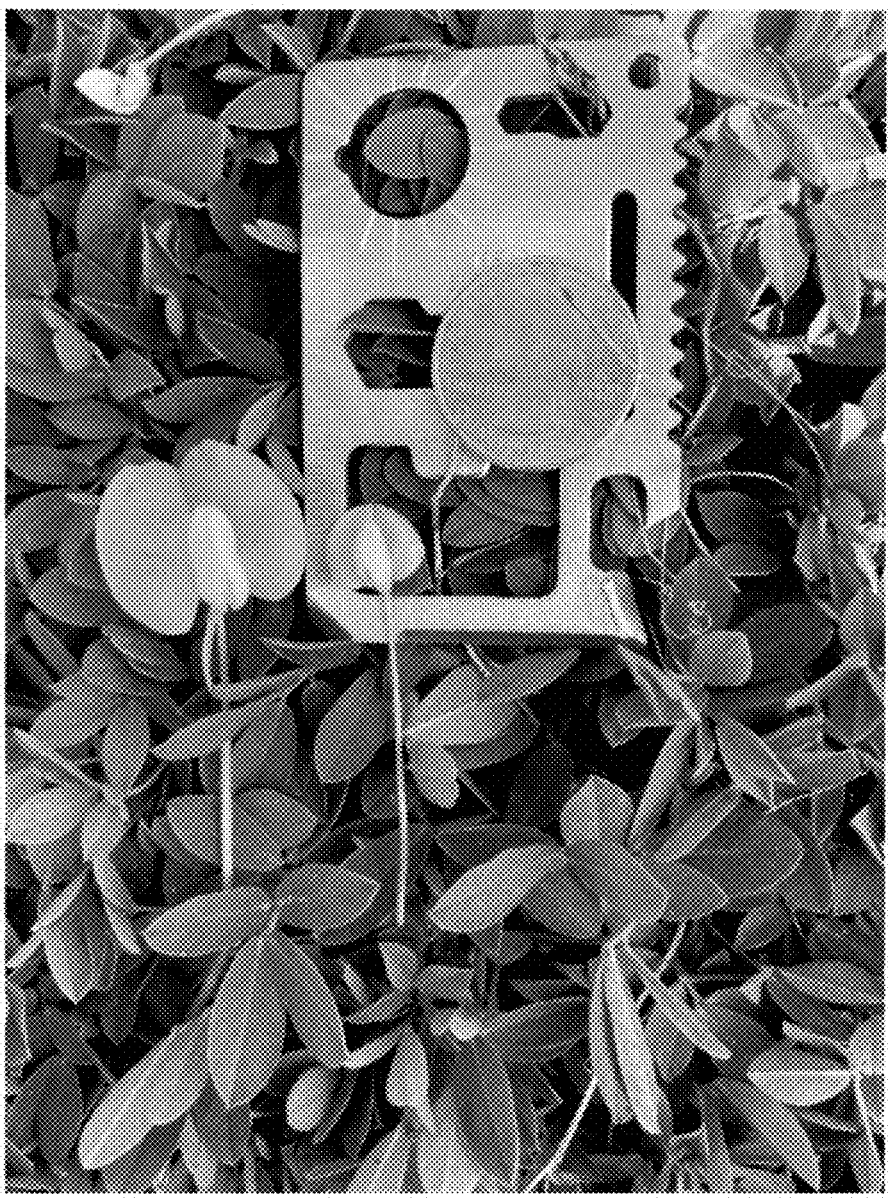
FIG. 4 shows the light-yellow color and small flower size of 'Murphy's Pintoi' (right), compared to the orange color and larger flower size of rhizoma perennial peanut (*A. glabrata*) (left).
Figure 5:
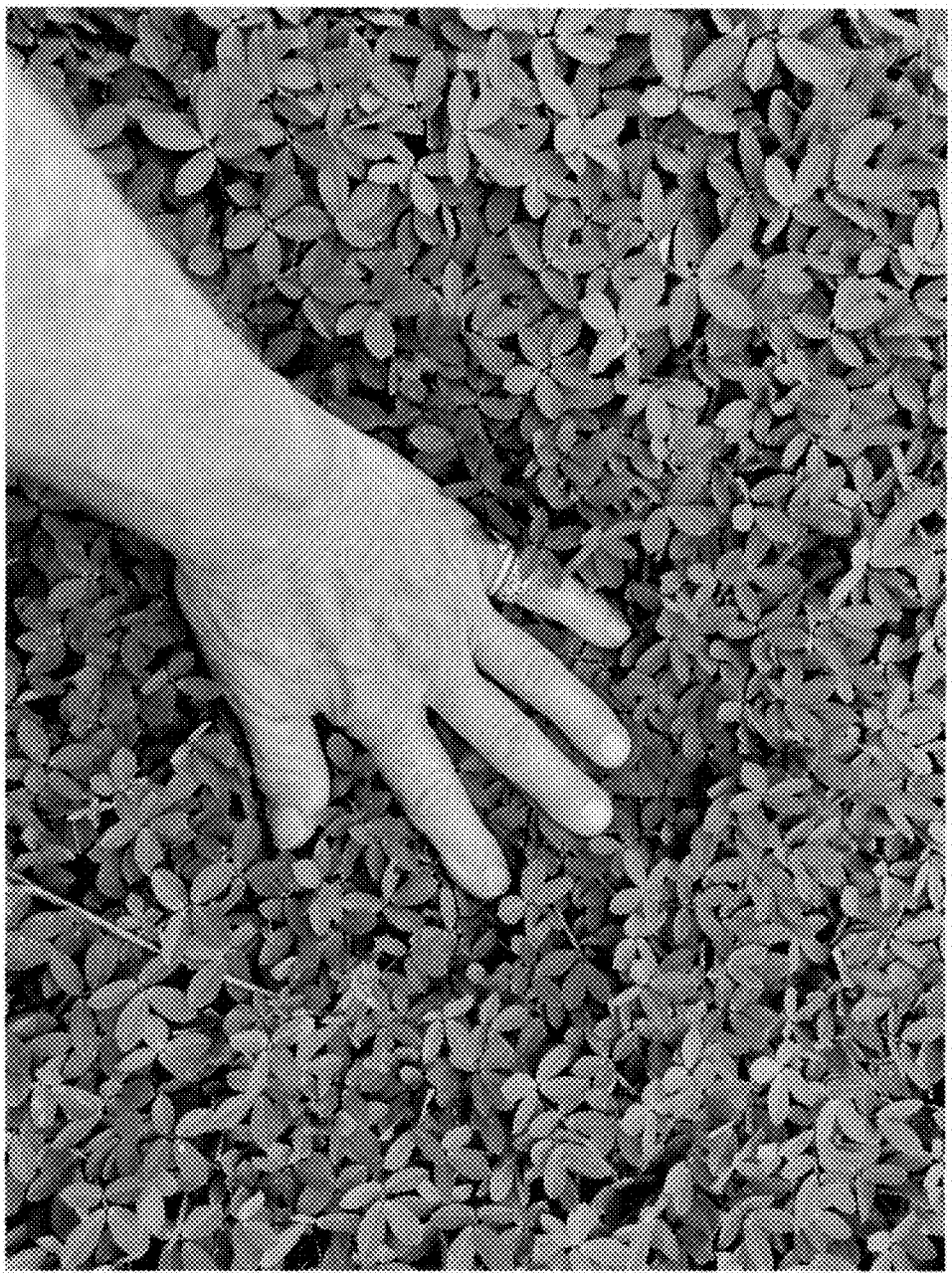
FIG. 5 demonstrates the dense and short growing habit of 'Murphy's Pintoi'.
Figure 6:
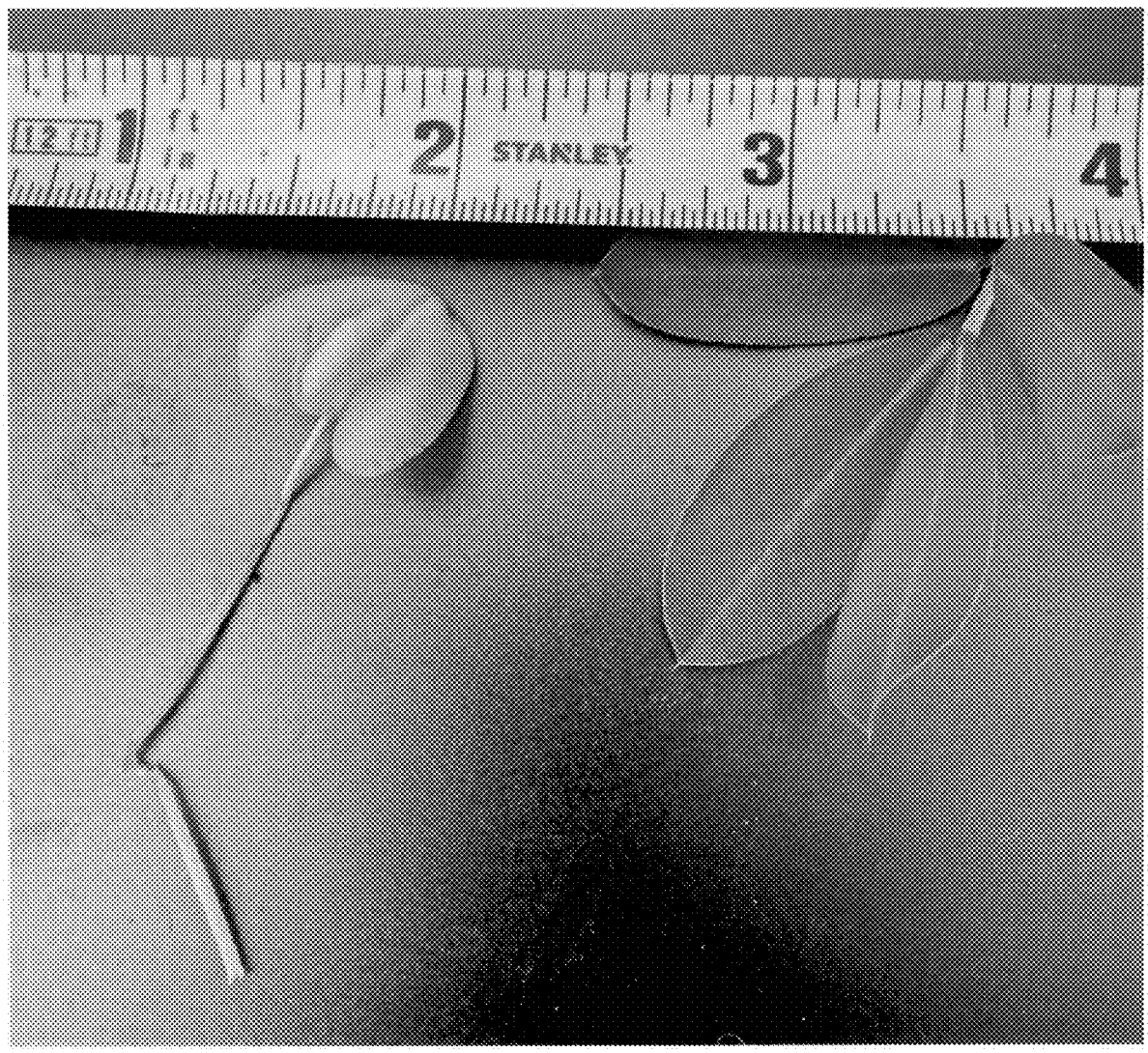
FIG. 6 shows the size of a flower of 'Murphy's Pintoi' relative to its leaf size.

Detailed observations were made under full sun conditions in the middle of the day with average temperatures of 85 degrees F. Color references are to The R.H.S. Colour Chart of The Royal Horticultural Society of London (R.H.S.), 5th Edition. The following detailed description of 'Murphy's Pintoi' was obtained in June 2024 in Quincy, Florida from five-year-old field grown plants and in July 2024 in Greensboro, Florida from two-year-old greenhouse grown plants.

BOTANICAL DESCRIPTION

Botanical classification:

*Family*.—Fabaceae.

*Botanical name*.—*Arachis pintoi*.

*Common name*.—Perennial Peanut.

*Cultivar*.—'Murphy's Pintoi'.

Plant description:

*Plant type*.—Stoloniferous perennial creeping legume.

*Growth habit*.—Low growing, prostrate, compact and dense; growth habit is further characterized by one main (mature) stem and secondary stems, as well as stolons.

*Height from soil level to top of foliar plane*.—Approximately 1 to 2 inches.

*Plant diameter*.—As a creeping stoloniferous legume, plant diameter is restricted by the open-area available for establishment.

*Growth rate*.—Rapid, at least 30.0 cm in diameter of new growth annually.

*Stem color*.—Immature stems: 141C (yellowish green) and some 133A (dark bluish green). Mature stems: 133A (dark bluish green).

*Internode length*.—Average 3.0 cm.

*Stolon length*.—14.0 cm to 18.0 cm until the first true leaf stage, average 16.0 cm.

*Stolon diameter*.—3.0 mm to 4.0 mm, average 3.5 mm.

*Stolon texture*.—Pubescent.

*Stolon color*.—N199A (grey brown).

*Stolon shape*.—Flat.

Propagation and roots:

*Type of cuttings*.—Vegetative by single-node stolons.

*Root description*.—Tap rooted, with secondary stolons and some fibrous rooting.

*Root habit*.—Stoloniferous and spreading rapidly.

*Root color*.—164B (orange).

Foliage description:

*Type*.—Tetrafoliolate, partipinate leaflets.

*Arrangement*.—Alternate.

*Attachment*.—Petiolate.

*Leaves*.—Leaflet shape: Ovate. Leaflet length: Upper leaflets: 1.4 cm to 1.6 cm, average 1.5 cm. Lower leaflets: 1.4 cm to 1.5 cm, average 1.45 cm. Leaflet width: Upper leaflets: 0.8 cm. Lower leaflets: 0.6 cm to 0.7 cm, average 0.65 cm. Leaflet position at broadest point: Towards apex. Apex shape: Rounded at the apex. Base shape: Obtuse. Texture (upper surface): Smooth, very sparse uniseriate trichrome. Texture (lower surface): Uniseriate trichrome, ciliate. Margins: Multi-seriate, slightly sinuate. Color (fully expanded leaves): Upper surface: 137A (moderate olive green). Lower surface: 137B (moderate olive green) to 137C (moderate yellow green). Color: (immature leaves): Upper surface: 146A (moderate olive green). Lower surface: 146C (moderate yellow green). Leaf sheen (both upper and lower surfaces): Matte. Venation pattern: Pinnate. Venation color: Upper surface: 137A (green). Lower surface: 137C (green).

Petiole.—Shape: Non-circular, flat. Length: 1.8 cm to 2.0 cm, average 1.85 cm. Diameter: Flat side: 0.57 mm to 0.67 mm, average 0.63 mm. Wider side: 1.08 mm to 1.24 mm, average 1.1 mm. Color: 144A (yellow green). Texture: Pubescent.

Flower description:

*Type*.—Papilionaceous flowers composed of five modified petals; banner, which is composed of one modified petal; two wings, which are composed of one modified petal each; and one keel, which is composed of two modified petals.

*Arrangement*.—Born on short axillary racemes.

*Flowering season*.—Late June to August.

*Habit*.—Sparse, few flowers occurring at Latitude 30-31.

*Longevity*.—Typically one day.

*Diameter*.—1.7 cm to 2.0 cm.

*Depth* (*or length*).—1.5 cm to 1.6 cm.

*Banner*.—Color: Front surface: 6B (greenish yellow). Back surface: 4A (greenish yellow). Quantity: 1 per flower. Length: 1.3 cm to 1.5 cm. Width: 1.4 cm to 1.5 cm. Margin: Entire. Texture: Smooth.

*Wings*.—Color: 7A (greenish yellow). Quantity: 2 per flower. Length: 8.0 mm to 9.0 mm. Width: 4.0 mm to 5.0 mm. Margin: Entire. Texture: Smooth.

*Keels*.—Color: 2C (light yellow green) to 2D (pale greenish yellow). Quantity: 1 per flower. Length: 4.0 mm to 6.0 mm. Margin: Entire. Texture: Smooth.

*Sepals*.—Color: 160C (greenish yellow) to 160D (pale yellow). Quantity: 2 per flower. Shape: One large acuminate sepal, and one small acicular sepal. Acuminate sepal: Length: 4.53 mm to 4.7 mm, average 4.61 mm. Width: 2.19 mm to 2.41 mm, average 2.3 mm. Acicular sepal: Length: 4.08 mm to 5.7 mm, average 4.7 mm. Width: 1.07 mm to 1.2 mm, average 1.12 mm. Apex: Acuminate sepal: Sublate with 3 teeth. Acicular sepal: Pointed. Margin: Entire. Texture: Pubescent.

*Peduncle*.—Color: 150C (yellow-green) near the flower and 159A (yellowish pink) near the stem. Length: 10.2 cm to 12.0 cm, average 11.1 cm. Diameter: 0.76 mm to 0.8 mm, average 0.78 mm. Texture: Pubescent.

*Male reproductive organs*.—Anther number: 8.Filament length: 2.3 mm to 3.3 mm, average 2.8 mm.

Disease and insect resistance: No evidence of Peanut Stunt Virus or Leaf Scorch has been observed compared to the industry standard *A. pintoi* 'Golden Glory' which is highly susceptible.

Cold tolerance: AHS Plant Heat Zone Map 9A (can overwinter in North Florida).

Nut description: Plants of 'Murphy's Pintoi' have not been observed to produce nuts.

COMPARISON WITH KNOWN CULTIVAR

When compared to 'Golden Glory' (unpatented), 'Murphy's Pintoi' has darker green leaves that are more elliptic in shape, whereas 'Golden Glory' has lighter green leaves that are more rounded in shape. Additionally, 'Murphy's Pintoi' is less susceptible to Peanut Stunt Virus and Leaf Scorch compared to 'Golden Glory'. Further, 'Murphy's Pintoi' has a very compact and dense growth habit, whereas 'Golden Glory' is less dense and has a more open foliage canopy.

What is claimed is:

1. A new and distinct cultivar of *Arachis pintoi* plant named 'Murphy's Pintoi', as illustrated and described herein.

* * * * *